(12) United States Patent
Kim et al.

(10) Patent No.: US 12,171,958 B2
(45) Date of Patent: Dec. 24, 2024

(54) METHOD FOR PREPARING A STEERABLE MEDICAL DEVICE WITH BRAIDED STRUCTURE

(71) Applicants: BOARD OF REGENTS OF THE UNIVERSITY OF TEXAS SYSTEM, Austin, TX (US); XCATH, INC., Houston, TX (US)

(72) Inventors: Daniel H. Kim, Houston, TX (US); Dong Suk Shin, Houston, TX (US); Viljar Palmre, Pearland, TX (US); Younghee Shim, Houston, TX (US)

(73) Assignees: BOARD OF REGENTS OF THE UNIVERSITY OF TEXAS SYSTEM, Austin, TX (US); XCATH, INC., Houston, TX (US)

( * ) Notice: Subject to any disclaimer, the term of this patent is extended or adjusted under 35 U.S.C. 154(b) by 442 days.

(21) Appl. No.: 17/553,371

(22) Filed: Dec. 16, 2021

(65) Prior Publication Data
US 2022/0105315 A1 Apr. 7, 2022

Related U.S. Application Data

(62) Division of application No. 16/478,425, filed as application No. PCT/US2018/044057 on Jul. 27, 2018, now Pat. No. 11,229,775.

(Continued)

(51) Int. Cl.
*A61M 25/00* (2006.01)
*A61L 29/02* (2006.01)
(Continued)

(52) U.S. Cl.
CPC ......... *A61M 25/0158* (2013.01); *A61L 29/02* (2013.01); *A61L 29/041* (2013.01);
(Continued)

(58) Field of Classification Search
CPC .......... A61M 25/0045; A61M 25/0052; A61M 2025/0058; A61M 2025/0063;
(Continued)

(56) References Cited

U.S. PATENT DOCUMENTS

| 5,964,971 A | * | 10/1999 | Lunn | A61M 25/005 156/149 |
| 6,314,856 B1 | * | 11/2001 | Keith | D04C 3/48 87/8 |

(Continued)

FOREIGN PATENT DOCUMENTS

| JP | 2007209554 A | 8/2007 |
| JP | 2012-139503 A | 7/2012 |

OTHER PUBLICATIONS

PCT/US2018/044057, International Search Report dated Nov. 7, 2018, 15 pages.

(Continued)

*Primary Examiner* — Donghai D Nguyen
(74) *Attorney, Agent, or Firm* — Patterson + Sheridan, LLP

(57) ABSTRACT

An elongate, flexible, medical device having distal and proximal ends, including an inner member having a proximal and distal end, a support member extending around the inner member between the proximal and distal end, a plurality of electrically-conductive wires, each braided with the support member having a proximal and distal end, an outer member surrounding the inner member, the support member, and the plurality of electrically-conductive wires and an actuator including a polymer electrolyte layer secured adjacent to the distal end of the elongate, flexible inner member and defining an exterior surface, electrodes distributed about the exterior of the polymer electrolyte layer. The distal end of one of the electrically-conductive wires is electrically connected to one of the electrodes. The (Continued)

polymer electrolyte layer is configured to deform asymmetrically in response to the application of an electrical signal through the plurality of electrically-conductive wires to the plurality of electrodes.

14 Claims, 9 Drawing Sheets

Related U.S. Application Data

(60) Provisional application No. 62/539,338, filed on Jul. 31, 2017.

(51) Int. Cl.
  *A61L 29/04* (2006.01)
  *A61L 29/08* (2006.01)
  *A61L 29/14* (2006.01)
  *A61M 25/01* (2006.01)
  *A61B 1/005* (2006.01)
  *A61M 25/09* (2006.01)

(52) U.S. Cl.
  CPC ............ *A61L 29/085* (2013.01); *A61L 29/14* (2013.01); *A61M 25/0045* (2013.01); *A61M 25/0052* (2013.01); *A61B 1/0057* (2013.01); *A61M 2025/0058* (2013.01); *A61M 2025/0063* (2013.01); *A61M 2025/09133* (2013.01); *A61M 2205/0238* (2013.01); *A61M 2205/0283* (2013.01)

(58) Field of Classification Search
  CPC .. A61M 2205/0238; A61M 2205/0283; A61B 1/0057; Y10T 29/49174
  See application file for complete search history.

(56) References Cited

U.S. PATENT DOCUMENTS

| | | | |
|---|---|---|---|
| 6,464,684 B1 | 10/2002 | Galdonik | |
| 7,909,844 B2 * | 3/2011 | Alkhatib | A61M 25/1006 604/99.01 |
| 9,147,825 B2 * | 9/2015 | Kim | H10N 30/87 |
| 9,364,635 B2 | 6/2016 | Wang et al. | |
| 2006/0111618 A1 | 5/2006 | Couvillon | |
| 2012/0172714 A1 | 7/2012 | Govari et al. | |
| 2013/0253424 A1 | 9/2013 | Kim et al. | |

OTHER PUBLICATIONS

Taiwanese Patent Application No. 107126074, Office Action and Search Report w/English translation, Aug. 8, 2019, 16 pages.
Canadian Patent Application No. 3,039,267, Office Action dated Feb. 18, 2020, 5 pages.
Canadian Patent Application No. 3,039,267, Office Action dated Jul. 15, 2020, 3 pages.
Australian Application No. 2018311843, Examination Report No. 1 dated Feb. 26, 2020, 4 pages.
Japanese Application No. 2019-520901, Office Action dated Jun. 30, 2020, 6 pages.
Korean Patent Application No. 10-2019-7010799, Notice of Grounds for Rejection dated Jan. 16, 2020, 6 pages.
European Patent Application No. 18841377.7, Extended European Search Report dated Aug. 24, 20, 6 pages.
Chinese Application No. 201880003922.4, Office Action dated Mar. 15, 2021 including English translation, 29 pages.

* cited by examiner

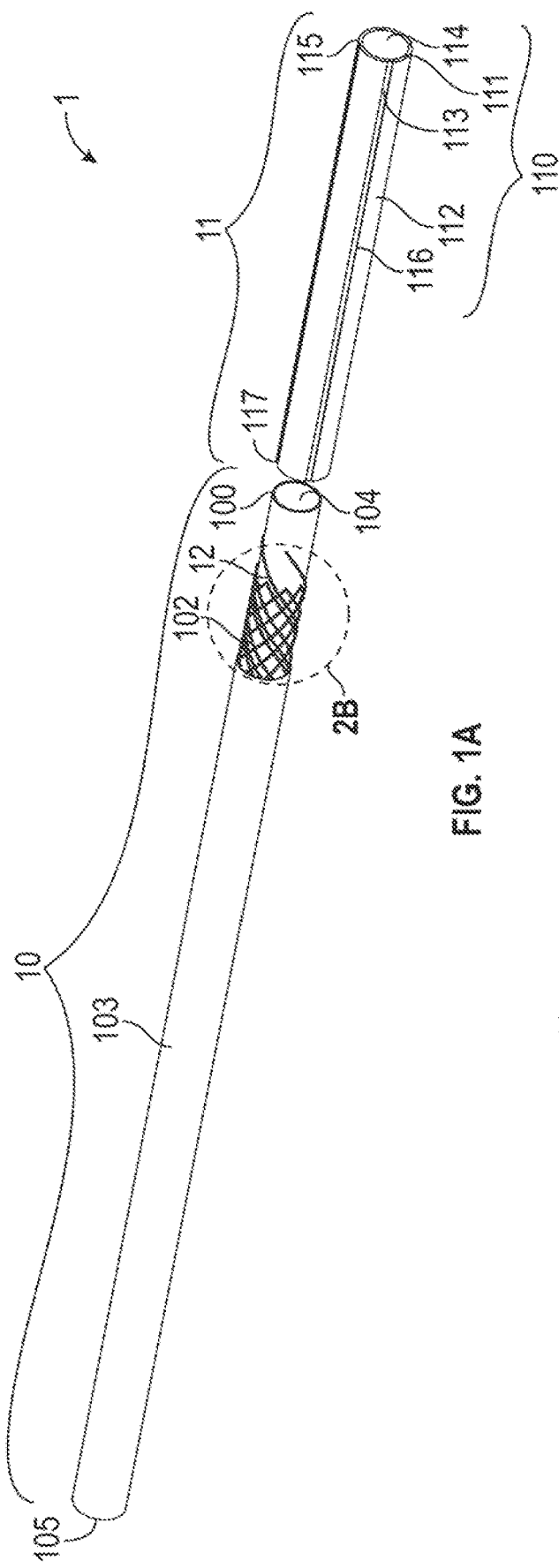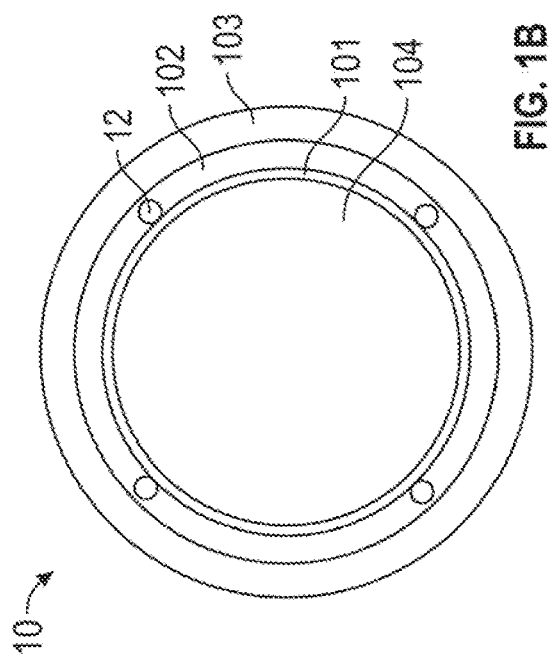
FIG. 1A
FIG. 1B

METHOD FOR PREPARING A STEERABLE MEDICAL DEVICE WITH BRAIDED STRUCTURE

CROSS REFERENCE TO RELATED APPLICATIONS

This application is a divisional patent application of U.S. application Ser. No. 16/478,425, filed on Jul. 27, 2018, and claims priority to PCT Application No. PCT/US17/16513 filed on Feb. 2, 2017, which is fully incorporated herein by reference in its entirety.

BACKGROUND

Field

The disclosure herein relates to a steerable intraluminal medical device and, more particularly, to a flexible, narrow medical device (such as a micro-catheter) introduced into and controllably moved through lumens of a body. The medical device may include an electrically-actuatable bendable portion at a distal, leading end thereof, that can be selectively manipulated for steering the medical device to a targeted anatomical location within a body.

Discussion of the Related Art

Intraluminal medical devices have various structures depending on the location of their intended deployment within the body and the methods of treatment using the devices. Intraluminal devices generally include of a very slender, i.e., very small in cross section, and flexible tube that can be inserted into and guided through a lumen such as an artery or a vein, or a bodily passageway such as a throat, a urethra, a bodily orifice or some other anatomical passage. Examples of such medical devices include syringes, endoscopes, catheters, guide wires and other surgical instruments.

Some medical devices include a portion configured for being introduced into a body that generally comprises a flexible material that is easily bent by application of external force. In some medical devices, a distal, leading end (usually inserted first) may be selectively bent in a desired direction through manipulation of a steering mechanism by the user. The medical device can be inserted into a targeted lumen or bodily passage and moved to dispose a distal end of the medical device at a desired location in the body.

To facilitate directional control of such a medical device, there are a small number of new catheters employing electroactive polymers (EAP) in their bending mechanisms, so that the shape of electroactive polymers (EAP) can be changed by the operator during use of the device, such as the use thereof during surgery. Such shape-changing ability allows at least portions of these catheters to be adjusted or changed by the surgeon during a procedure to fit the anatomy of the patient, which normally varies due to disease, body type, genetics and other factors. Exemplary catheters having electroactive polymers (EAPs) to change the shape of the catheter, selectively bend or provide variable stiffness at different locations on the catheter are disclosed in U.S. Pat. No. 7,766,896 B2, US 2007/0250036 A1, US8,414,632 B2, and U.S. Pat. No. 6,679,836 B2.

Further, in order to operate one or more elements on a distal portion of such EAP catheters, one or more electrically-conductive wires or conductors need to be integrated between the inner liner and outer jacket surfaces of their catheter shafts that extend longitudinally. Incorporating these wires or elements into or onto thin-walled tubular structures like catheter shafts or deflectable sheaths, is challenging because the wires used herein are too small (around 25 microns or smaller) to assemble into the catheter using conventional mechanical assembly techniques. More specifically, these electrically-conductive wires are very sensitive to electrostatic forces, and thus they are drawn electrostatically toward any nearby surface by electrostatic forces, especially toward the polymer surface of the liner of the catheter shaft to which the wires are to be integrated, which makes them vulnerable to be damage and causes them to be difficult to incorporate into the catheter shaft. In view of this, there is a need for improvement of EAP catheter structures and manufacturing methods thereof.

SUMMARY

Embodiments of the steerable medical device provide an improved braided structure to firmly secure the wires in the catheter, and provide improved steering control and intra-body positioning of an actuation part (e.g., a catheter) of a medical device wherein the actuation part is adapted to be introduced into a lumen or a bodily passage of a body and manipulated while being extended for movement into and through the lumen and/or bodily passage to dispose a distal end of the actuation part of the medical device at a desired anatomical location within the body. Also, embodiments of the manufacturing method provide more simplified and efficient process for preparing the steerable medical device.

In one embodiment, an elongate, flexible, medical device having a distal end and a proximal end, includes an elongate, flexible inner member having a proximal end and a distal end, a support member extending around the inner member intermediate the proximal end and the distal end thereof, a plurality of electrically-conductive wires, each being braided with the support member and having a proximal end and a distal end, an outer member surrounding the inner member, the support member, and the plurality of electrically-conductive wires and at least one ionic electroactive polymer actuator, the actuator including at least one polymer electrolyte layer secured adjacent to the distal end of the elongate, flexible inner member and defining an exterior surface, a plurality of electrodes circumferentially distributed about the exterior surface of at least one polymer electrolyte layer, and wherein at least one of the plurality of electrically-conductive wires, t the distal end thereof, is electrically connected to one of the electrodes, and, the at least one polymer electrolyte layer is configured to deform asymmetrically in response to the application of an electrical signal through at least one of the plurality of electrically-conductive wires to at least one of the plurality of electrodes.

One embodiment of a steerable medical device is provided herein, comprising: an elongate, flexible portion, at least one ionic electroactive polymer actuator, and a plurality of electrically-conductive wires. The elongate, flexible portion has a distal end and a proximal end and further comprises: an elongate, flexible inner member, an outer member, and a support member. The elongate, flexible inner member has a proximal end and a distal end disposed to couple with the at least one polymer electrolyte layer of the ionic electroactive polymer actuator as discussed below. The outer member surrounds the inner member, the support member and the plurality of electrically-conductive wires, and the support member is wrapped around the inner member intermediate the proximal end and the distal end. The ionic electroactive polymer actuator, as will be discussed in greater detail below, is an actuator comprising at least one polymer electrolyte layer in which cations are free to migrate in response to an imposed electrical field. The polymer electrolyte layer is secured adjacent to the distal end of the elongate, flexible inner member, and further defines an exterior surface. The electrical field is provided through energization of a plurality of electrodes disposed and spaced from one another on the polymer electrolyte layer. The plurality of electrodes is circumferentially distributed about the exterior surface of at least one polymer electrolyte layer. Each of the plurality of electrodes may be connected to a source of electrical potential through one or more electrically-conductive wires such as, for example, a metal wire, being braided with the support member and having a proximal end coupled to the source of electrical potential and a distal end coupled to the electrode. Thus, the polymer electrolyte layer may deform asymmetrically in response to the application of an electrical signal through at least one of the plurality of electrically-conductive wires to at least one of the plurality of electrodes.

In some embodiments, the polymer electrolyte layer may comprise a polymer host and an electrolyte as solvent therein. The polymer may comprise, but is not limited to, fluoropolymers and intrinsically conducting polymers. In an exemplary embodiment, the fluoropolymers may comprise perfluorinated ionomers, polyvinylidene difluoride (PVDF) or co-polymer thereof (e.g. Poly(vinylidene fluoride-co-hexafluoropropylene) (PVDF-HFP), but are not limited to these polymers. In another exemplary embodiment, the intrinsically conducting polymers may comprise, but are not limited to, polyaniline (PANI), polypyrrole (Ppy), poly(3,4-ethylenedioxythiophene) (PEDOT), poly(p-phenylene sulfide) (PPS) or the combination thereof. In yet another embodiment, the electrolyte may be water or an ionic liquid. Exemplary example of the ionic liquid may include, but are not limited to, 1-ethyl-3-methylimidazolium tetrafluoroborate (EMI-BF4), 1-ethyl-3-methylimidazolium bis(trifluoromethylsulfonyl)imide (EMI-TFSI), 1-ethyl-3-methylimidazolium trifluoromethanesulfonate (EMITf) or the combination thereof.

In one embodiment of the medical device, each of the electrodes may comprise materials such as platinum, gold, carbon-based material or their combination thereof. Exemplary examples of the carbon-based material may comprise, but are not limited to, carbide-derived carbon, carbon nanotube(s), graphene, a composite of carbide-derived carbon and polymer electrolyte material (e.g. ionomer), and a composite of carbon nanotube and polymer electrolyte material (e.g. ionomer). In other embodiments, each of the electrodes may be a multilayered structure. For example, the electrode may comprise at least two layers in which one layer is a carbon-electrode layer comprising one or more carbon-based materials as described above while the other is a gold-electrode layer being disposed on a surface of the carbon-electrode layer.

In one embodiment of the medical device, the ionic electroactive polymer actuator may comprise a plurality of individual, and electrically isolated from one another, angularly distributed electrodes equi-angularly distributed about the exterior surface of the polymer electrolyte layer. In one embodiment of the medical device, the ionic electroactive polymer actuator may be included at the distal end of a bendable portion of a catheter. For example, but not by way of limitation, the bendable portion of the medical device may, in one embodiment, comprise four angularly-distributed electrodes that are separated, at their centerlines, one from the others by about 90 degrees (1.571 radians). As another example, but not by way of limitation, the ionic electroactive polymer actuator may comprise eight angularly-distributed electrodes that are separated, at their centerlines, by about 45 degrees (0.785 radians) from each other. In yet another example, the ionic electroactive polymer actuator 110 may comprise three angularly-distributed electrodes that are separated, at their centerlines, one from the others by about 120 degrees (2.094 radians). It will be understood that each of the plurality of electrodes occupies a circumferential span about the surface of the polymer electrolyte layer, and that the "angular separation" may therefore be stated in terms of the centerlines of the electrodes instead of in terms of the adjacent edges of the electrodes, which will be much closer to the adjacent edge of the adjacent electrode than will be their centerlines. In some embodiments of the medical device, the electrodes are spaced in a manner to provide a substantial gap as insulation channels intermediate adjacent electrodes. In other embodiments, the polymer electrolyte layer may further define an inner surface corresponding to the exterior surface and at least an internal electrode provided on the inner surface.

In one embodiment of the medical device, the support member may be a reinforcing mesh, a wire-braided matrix, or a coil formed from one or more reinforcement materials wound in a braided or other helical configuration around the inner member. Exemplary examples of reinforcement materials may comprise, but are not limited to, one or more round or flat (e.g., rectangular, elliptical, or flat oval) wires, filaments, strands or the like formed from metal (e.g. stainless steel), plastic (e.g. polyether ether ketone (PEEK)), glass, woven or twisted fibers (e.g. aramid) or composite materials.

In one embodiment of the medical device, the inner member and the at least one polymer electrolyte layer may further form a bore therein for receiving and passing through an elongate structure (e.g. a guidewire) inserted therein, and the polymer electrolyte layer is secured adjacent to the distal end of the inner member with the bore of the polymer electrolyte layer aligned with the bore of the inner member, so that the elongate structure may be fed through the bore of the inner member and the bore of the polymer electrolyte layer to extend out from the ionic electroactive polymer actuator.

In one embodiment of the medical device, each of the plurality of electrically-conductive wires may further comprise an insulation coating covered thereon to further insulate them from the outer member and the support member.

In some embodiments, the medical device may further comprise conductive bridges extending along the polymer electrolyte layer, each conductive bridge electrically connected to one of each of the electrodes. The distal end of each electrically-conductive wire can be coupled to the conductive bridge to electrically connect the ionic electroactive polymer actuator to one of the electrically-conductive wires, and thus to a source of electricity.

In other aspects, a method for preparing the above-mentioned medical device is provided herein, includes: providing ionic electroactive polymer actuator comprising a tubular electroactive polymer layer having a bore and an exterior surface wherein a plurality of electrodes circumferentially distributed about the exterior surface of the tubular electroactive polymer layer; providing an elongate, flexible inner member having a proximal end and a distal end, wherein the distal end extends into a portion of the bore of the tubular polymer electrolyte layer; providing a plurality of electrically-conductive wires, each having a proximal end and a distal end; braiding each electrically-conductive wire with the support member; surrounding the inner member intermediate of the proximal end and the distal end of the inner member with the support member braided with the electrically-conductive wires; providing an outer member having a proximal end and a distal end to surround the inner member and the support member braided with the electrically-conductive wires; providing a heat-shrink tube; covering the ionic electroactive polymer actuator, the outer member, the support member braided with the electrically-conductive wires and the inner member therein with the heat-shrink tube; and heating the heat-shrink tube to cause shrinkage of the polymer film, so that the ionic electroactive polymer actuator, the outer member, the support member braided with the electrically-conductive wires and the inner member therein are secured together.

In some embodiments, the methods may comprise a step of electrically contacting the distal end of each electrically-conductive wire to the electrodes directly or indirectly. For example, in one embodiment, the distal end of one of each electrically-conductive wires can be coupled to a surface of at least one of the electrodes directly. In another embodiment, one or more conductive bridges can be formed and extend from each of the electrodes and along the tubular polymer electrolyte layer, so that the distal end of each electrically-conductive wire can be indirectly coupled to an electrode via the conductive bridge.

BRIEF DESCRIPTION OF THE DRAWINGS

The appended illustrative drawings provide a further understanding of embodiments and are incorporated into and constitute a part of this application and, together with the written description, serve to explain the present invention. The appended drawings are briefly described as follows.

FIG. 1A is an exploded view of a catheter comprising an elongate, flexible portion and a bendable portion according to one embodiment.

FIG. 1B is a cross-sectional view of the elongate, flexible portion of the catheter in FIG. 1A.

FIGS. 5A to 5E illustrates the integration of the elongate, flexible portion and the bendable portion of a catheter in FIG. 1A according to one embodiment, wherein:

FIG. 5A is a schematic view illustrating the separate liner and the ionic electroactive polymer actuator;

FIG. 5B is a schematic view illustrating that the inner liner is fitted into a portion of the bore of the ionic electroactive polymer actuator;

FIG. 5C is a schematic view illustrating interconnection of the electrically-conductive wires and the electrodes on the ionic electroactive polymer actuator that is indicated in solid lines to better reveal details of the components therein.

FIG. 5D is a schematic view illustrating that the support member braided with electrically-conductive wires is attached on the liner fitted into a portion of the bore of the ionic electroactive polymer actuator; and FIG. 5E is a schematic view illustrating that the outer jacket is positioned over the support member braided with electrically-conductive wires.

DETAILED DESCRIPTION OF THE PREFERRED EMBODIMENTS

Figure 2A:
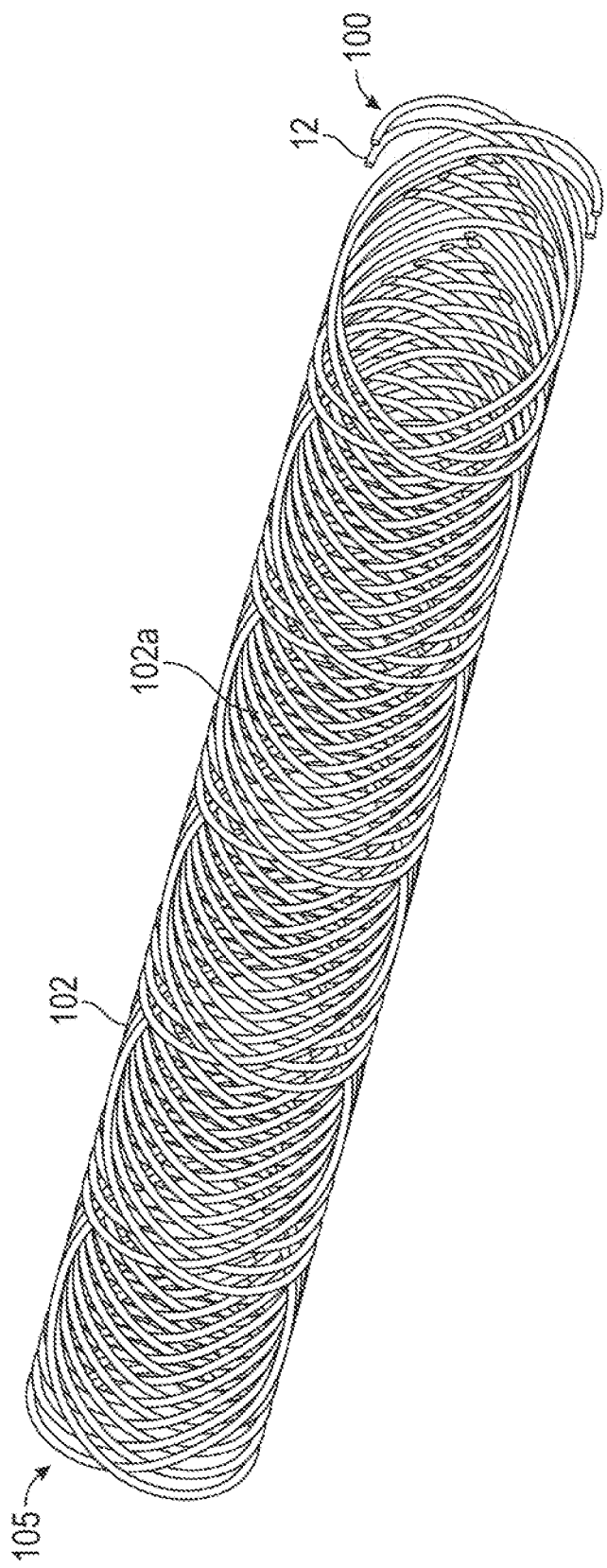
FIG. 2A is a perspective view illustrating the overall support member and the electrically-conductive wires in FIG. 1A.

Medical devices such as catheters may be sufficiently slender for being inserted into a lumen such as an artery, a vein, a throat, an ear canal, a nasal passage, a urethra or any of other lumens or bodily passages. For example, slender catheters (also referred to as micro-catheters) enable physicians to perform non-invasive surgery requiring a substantially shortened recovery period by preventing the need for cutting a large opening into a subject or a patient to provide local access for performing a surgical procedure or medical operation.

As used herein, the terms "subject" or "patient" refer to the recipient of a medical intervention with the device. In certain aspects, the patient is a human patient. In other aspects, the patient is a companion, sporting, domestic or livestock animal.

As used herein, the terms "ionic electroactive polymer actuator" refer to a component of a medical device comprising a thin polymer electrolyte layer in which cations are free to migrate in response to an imposed electrical field and one or more electrodes disposed on the surface of the polymer electrolyte layer. As described herein, the "ionic electroactive polymer actuator" may be provided at the distal end forming a bendable portion of a medical device (e.g. a catheter tip) to be selectively bendable. More specifically, selective electrical energization of one or more electrodes causes the polymer electrolyte layer to deform as a result of contraction along a side or portion of the polymer electrolyte layer and/or swelling along a side or portion of the polymer electrolyte layer. It will be understood that cations within the polymer electrolyte layer will migrate towards an anodically energized electrode, and away from a cathodically energized electrode, while still remaining within the matrix of the polymer electrolyte layer. This causes the portion of the polymer electrolyte layer adjacent to an anodically energized electrode to swell and a portion of the polymer electrolyte layer adjacent to a cathodically energized electrode to contract, thereby causing the polymer electrolyte layer to bend. It will be also understood that coordinated control of electrical signals delivered to the electrodes through electrically-conductive wires can produce bending in an intended direction. In a relaxed or un-energized state, the polymer electrolyte layer of the ionic electroactive polymer actuator remains in its original form.

As used herein, the term "polymer electrolyte layer" refers to a layer or membrane comprising a polymer host and an electrolyte (e.g., a solvent such as, water or an ionic liquid). The polymer host may comprise, for example, but not by way of limitation, fluoropolymers and intrinsically conducting polymers. For example, the polymer electrolyte layer may comprise a porous polyvinylidene fluoride or polyvinylidene difluoride, a highly non-reactive thermoplastic fluoropolymer produced by the polymerization of vinylidene difluoride, and containing ionic liquid or salt water. Alternately, the polymer electrolyte may comprise a gel formed by polyvinylidene fluoride or polyvinylidene difluoride, propylene carbonate and an ionic liquid.

As used herein, the term "electrically-conductive wire" refers to a component that conducts electrical signals from a source of electricity to one or more of the plurality of electrodes to affect bending of the polymer electrolyte layer may comprise a noble metal for superior chemical stability and corrosion resistance. For example, but not by way of limitation, the electrically-conductive wires that deliver potential to selected electrodes to actuate the polymer electrolyte layer may comprise highly conductive platinum, a platinum alloy, silver or a silver alloy, or they may comprise gold or a gold alloy which, in addition to being chemically stable and corrosion resistant, is malleable and can be advantageously formed into very slender electrically-conductive wires or conduits having very low resistance to bending.

The following paragraphs describe certain embodiments of medical devices that can be used to perform or to enable the performance of surgical operations using the same, and methods that can be used to enable the preparation of such medical devices for same. It will be understood that other embodiments of medical devices and methods are within the scope of the claims appended herein below, and the illustration of such embodiments is not limiting of the present invention.

FIG. 1A illustrates one embodiment of a medical device, comprising an exploded view of a catheter 1. The catheter 1 comprises an elongate, flexible portion 10 to be extendable from a controller (not shown) and a bendable portion 11 disposed at the distal end 100 of the elongate, flexible portion 10. FIG. 1B is a cross-sectional view of the elongate, flexible portion 10 of the medical device in FIG. 1A. The elongate and flexible portion 10 further comprises a tubular inner liner 101, a support member 102, and an outer jacket 103. The bendable portion 11 includes an ionic electroactive polymer actuator 110 comprising a polymer electrolyte layer member 111 disposed adjacent to the inner liner 101 of the elongate, flexible portion 10 and centrally to a plurality of energizable electrodes 112. Each of the plurality of electrodes 112 that surrounds the exterior surface 113 of the polymer electrolyte layer 111 is connected to a distal end 120 one of a plurality of electrically-conductive wires 12 through which an electrical signal or current may be supplied to the connected electrode 112. The inner liner 101 and the polymer electrolyte layer 111 further form an interior bore 104, 114 respectively to guide an inserted guidewire (not shown) to a predetermined position within a lumen of the body. In one embodiment, the polymer electrolyte layer 111 is secured adjacent to the distal end 100 of the inner liner 101 with the bore 114 of the polymer electrolyte layer aligned with the bore 104 of the inner liner 101. The inserted guidewire may be thus fed from the proximal end 105 of the elongate, flexible portion 10 through the bores 104, 114 to the distal end 115 of the bendable portion 11.

The inner liner 101 is sufficiently slender to be inserted into a lumen (not shown) of a body (not shown), i.e., it has a sufficiently small cross section to allow this use. Also, the inner liner 101 is sufficiently flexible and substantially axially incompressible so that it can be advanced through a lumen having a winding pathway by pushing or driving the elongate, flexible portion 10 forward after the distal end 100 is introduced into the lumen of the body (not shown). In some exemplary examples, the inner liner 101 may be a lubricious liner which additionally is configured to provide strengthening and stiffening to the proximal portion of the catheter 1. The liner 101 can not only prevent the support member 102 thereon from being exposed on the inner surface of the catheter 1 and thus to the bore 104, but also can improve the lubricity of the catheter inner lumen surfaces (i.e. the wall surfaces of the bores 104, 114) to aid guidewire placement. In some exemplary examples, the inner liner 101 may be formed with a low friction polymer which comprises fluorocarbon (such as polytetrafluoroethylene (PTFE)), high density polyethylene, other low-friction polymers, or combinations thereof, but is not limited to this. The low friction polymer, such as PTFE, may be combined with another more rigid polymer, such as polyimide to increase the strength of the inner liner 101.

Figure 2B:
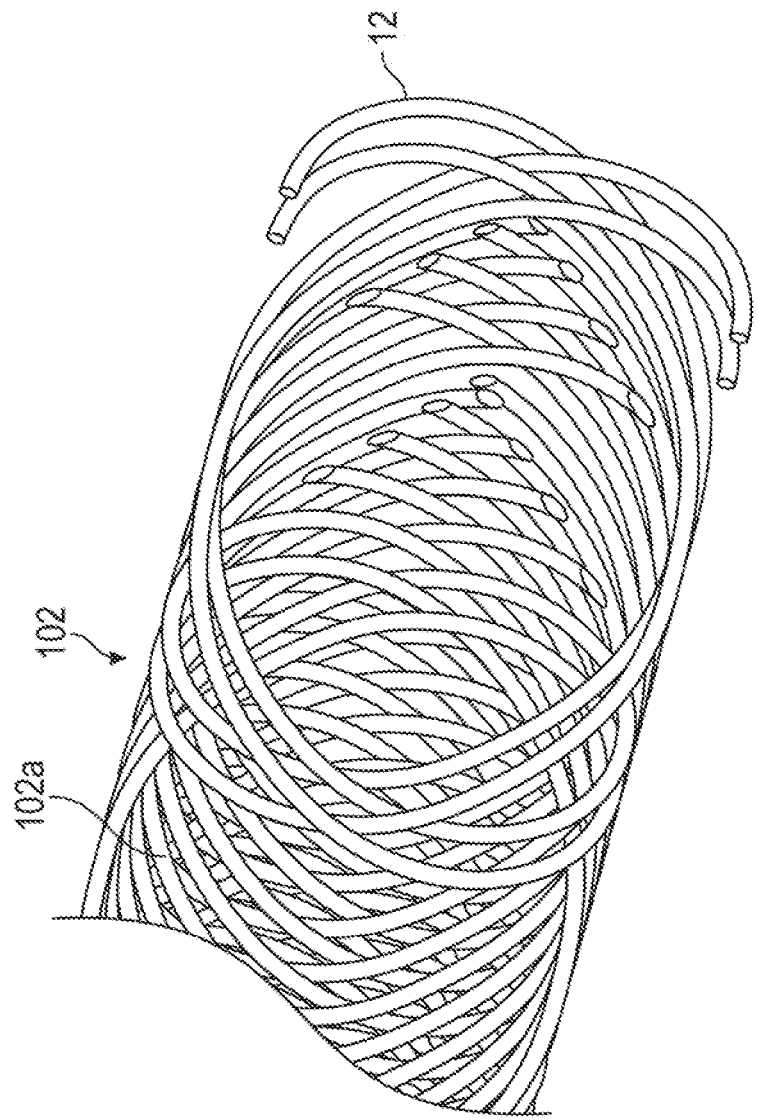
FIG. 2B is an enlarged view of a portion of the support member and the electrically-conductive wires in FIG. 1A.

FIG. 2A is an isometric of FIG. 1A view illustrating the overall support member and the electrically-conductive wires. FIG. 2B is an enlarged view of a portion of the support member and the electrically-conductive wires in FIG. 1A. Surrounding the liner 101 are the support member 102, and a plurality of electrically-conductive wires 12, that are integrally braided together to provide a fairly secured-incorporated braided structure, thereby reducing damage to the vulnerable electrically-conductive wires 12 during assembly and use of the catheter 1. Also, the support member 102 can provide enhanced structural rigidity and resistance to axial compression and enhanced resistance to torsional deformation of the elongate, flexible portion 10 for improved control and steerability of the catheter 1. The support member 102 may comprise, for example, but is not limited to a reinforcing mesh, a wire-braided matrix or a coil formed from one or more reinforcement materials 102a and the conductive wires 12 wound in a braided or other helical configuration around the inner liner 101. Exemplary examples of reinforcement materials 102a may include, but are not limited to, one or more round or flat (e.g., rectangular, elliptical, circular, ribbon, flat oval or other shape) wires, filaments, strands or the like formed from metal (e.g. stainless steel, Nitinol or tungsten), plastic (e.g. polyether ether ketone (PEEK), nylon), glass, woven or twisted fibers (e.g. aramid) or composite materials. Reinforcement materials 102a and arrangements thereof can be varied in size, number and pitch (spacing therebetween) along the length of the catheter 1 to achieve desired catheter handling characteristics. As shown in FIGS. 2A and 2B, the support member 102 may have reinforcement materials 102a formed at fixed winding pitch. Alternatively, the support member 102 may be formed in three or more sections of differing pitches. In one embodiment, the support member 102 may be provided with reinforcement materials 102a having a lower pitch (closer spacing) at the proximal end 105 to provide increased strength and a higher pitch (greater spacing) at the distal end 100 to provide increased kink resistance and flexibility.

Figure 3B:
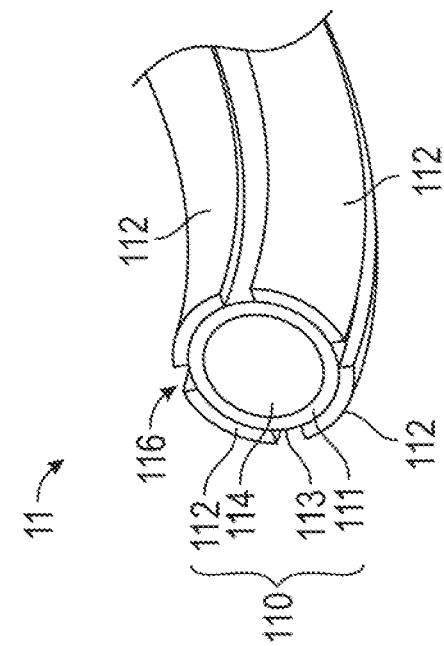
FIG. 3B is a perspective view of the bendable portion of FIG. 3A in the deformed or bending mode.
Figure 3D:
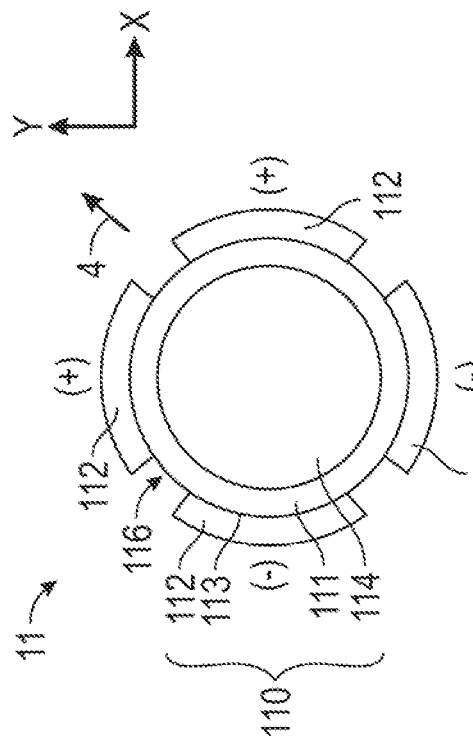
FIG. 3D is the cross-sectional view of the bendable portion of FIGS. 3A and 3B revealing another embodiment that a second selected set of four electrical signals applied to the circumferentially distributed electrodes disposed about the polymer electrolyte layer.
Figure 3A:
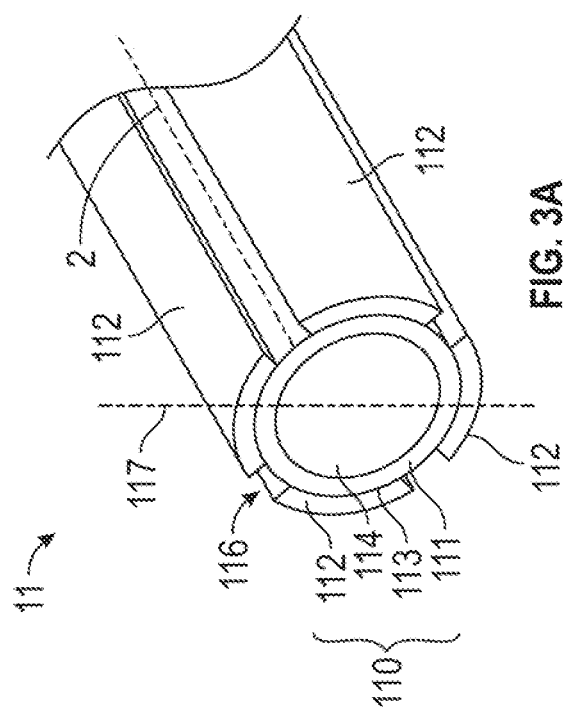
FIG. 3A is a perspective view of the bendable portion of one embodiment of FIG. 1A, illustrating the bendable portion in the straight mode.

FIG. 3A is a perspective view of the bendable portion 11 of the embodiment of the catheter of FIG. 1A, illustrating the bendable portion 11 in the straight mode. The bendable portion 11 includes an ionic electroactive polymer actuator 110 comprising a tubular polymer electrolyte layer 111 disposed adjacent to the distal end 100 of elongate, flexible portion 10 and centrally to an angularly-distributed plurality of energizable electrodes 112. Each of the plurality of electrodes 112 that together surround the exterior surface 113 of the polymer electrolyte layer 111 is connected to a distal end 120 of an electrically-conductive wire 12 through which an electrical signal or current may be supplied to the connected electrode 112. The polymer electrolyte layer 111 includes a bore 114 through which other elongate structures (e.g. a guidewire) may be inserted to position, control and/or actuate an end effector or surgical tool or instrument disposed at the distal end of the elongate structure. The bore 114 of the polymer electrolyte layer 111 is, in a relaxed or de-energized condition, centered about an axis 2.

In one embodiment, the angularly distributed electrodes 112 are equi-angularly distributed about the exterior surface 113 of the polymer electrolyte layer 111. For example, but not by way of limitation, the ionic electroactive polymer actuator 110 may, in the embodiment of FIG. 3A, comprise four angularly-distributed electrodes 112 that are separated, at their centerlines, one from the others by about 90 degrees (1.571 radians). It will be understood that each of the plurality of electrodes 112 occupies a circumferential span along the surface of the polymer electrolyte layer, and that the "angular separation" may therefore be stated in terms of the centerlines 117 of the electrodes instead of in terms of the adjacent edges of the electrodes, which will be much closer to the adjacent edge of the adjacent electrode. In some embodiments, the electrodes are spaced in a manner to provide a substantial gap as insulation channels 116 intermediate adjacent electrodes.

In one embodiment, the ionic electroactive polymer actuator 110 of FIG. 3A is an ionic polymer-metal composite (IPMC) actuator. In one embodiment, the ionic electroactive polymer actuator 110 includes a polymer electrolyte layer 111 made of PVDF-HFP that is impregnated with EMITF (as electrolyte). Alternatively, other embodiments of the ionic electroactive polymer actuator 110 of the catheter 1 may include a polymer electrolyte layer 111 that includes at least one of a perfluorinated ionomer such as Aciplex™ (available from Asahi Kasei Chemical Corp. of Tokyo, Japan), Flemion® (available from AGC Chemical Americas, Inc. of Exton, Pennsylvania, USA), fumapem® F-series (available from Fumatech BWT GmbH, Bietigheim-Bissingen, Federal Republic of Germany) or Nafion® (available from The Chemours Company of Wilmington, Delaware, USA).

In one embodiment, the electrodes 112 may include one of platinum, gold, a carbon-based material, or a combination (e.g. a composite) thereof. In other embodiments, the carbon-material may include, for example, but is not limited to, carbide-derived carbon (CDC), carbon nanotube (CNT), graphene, a composite of carbide-derived carbon and the polymer electrolyte layer 111, and a composite of carbon nanotube and the polymer electrolyte layer 111. In an exemplary embodiment, as shown in FIGS. 4A to 4D, the electrodes 112 are double-layered, and include: a composite layer 112a of carbon (CDC and/or CNT) and PVDF-HFP/EMITF and a gold layer 112b thereover. The electrodes 112 can be integrated on the exterior surface 113 of the polymer electrolyte layer 111 using any suitable techniques. For example, but not by way of limitation, metal electrodes 112 can be deposited (e.g. platinum or gold electrodes) thereon using an electrochemical process. Alternatively, the double-layered electrodes 112 can be prepared and integrated on the exterior surface 113 by the following steps: spraying the composite layer 112a on the exterior surface 113, spray coating a gold layer 112b on the composite layer 112a, followed by integrating the layers 112a, 112b using a reflow process. The detail of the reflow process is discussed in PCT Application No. PCT/US17/16513, which is fully incorporated herein by reference in its entirety.

The bendable portion 11 can be selectively and controllably deformed to a bent mode by selective energization of one or more of the plurality of electrodes 112, as will be explained in further detail below. FIG. 3B is an isometric view of the portion of the bendable portion 11 of FIG. 3A in the deformed or bending mode. Each of the plurality of electrodes 112 is connected to a distal end 120 of the electrically-conductive wire 12 through which an electrical signal may be applied to the electrodes 112 to which the wire 12 is connected, thereby causing metal cations within the polymer electrolyte layer 111 to move in a direction determined by the applied electrical signal. This cation migration produced by the applied electrical signal causes the polymer electrolyte layer 111 to swell in the portion of the polymer electrolyte layer 111 disposed proximal to the anode and to bend or warp in the direction of the remaining unswelled portion. As a result, the magnitude and the direction of bending deformation of the polymer electrolyte layer 111 of the ionic electroactive polymer actuator 110 can be controlled by strategically selecting the electrodes 112 to energize and by adjusting the electrical signal applied through the electrically-conductive wire 12 to those electrodes 112.

Alternately, in the event that the bendable portion 11 is observed to be in a deformed mode in the absence of the application of one or more electrical signals to one or more of the plurality of the electrodes 112, the magnitude of the observed deflection can be used to determine the magnitude and direction of an external force applied to the bendable portion 11 or, alternatively, in the event that the application of a known current to the electrodes 112 fails to produce an anticipated deformation of the bendable portion 11, the difference between the anticipated deformation and the actual deformation (if any) can be used as an indicator of the magnitude of an external force applied to the bendable portion 11 of the catheter 1.

Figure 3C:
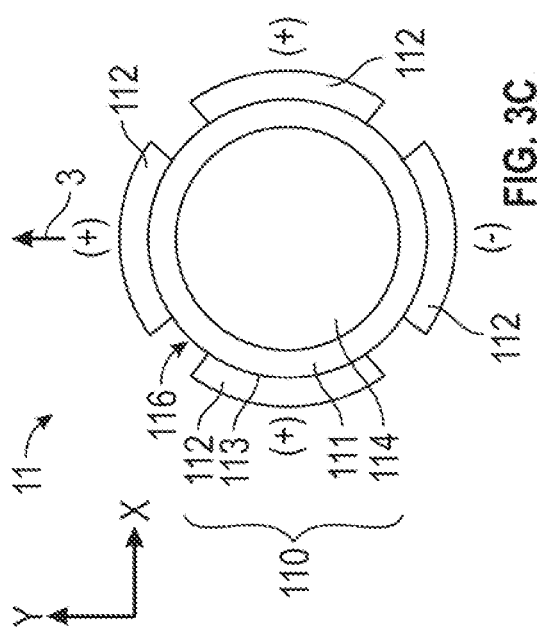
FIG. 3C is a cross-sectional view of the bendable portion of FIGS. 3A and 3B illustrating one embodiment that a first selected set of four electrical signals is applied to four circumferentially distributed electrodes disposed about the exterior surface of the polymer electrolyte layer to provide two degrees of freedom.

FIG. 3C is a cross-sectional view of the bendable portion 11 of FIGS. 3A and 3B illustrating one embodiment that a first selected set of four electrical signals is applied to four circumferentially distributed electrodes 112 disposed about the exterior surface 113 of the polymer electrolyte layer 111 to provide two degrees of freedom (e.g. bending along X-axis direction and/or Y-axis direction). FIG. 3C illustrates the electrical signals that may be applied to the plurality of angularly distributed electrodes 112 to impart bending of the bendable portion 11 in the direction of the arrow 3. It will be understood that the application of a positive charge (potential) on the electrodes 112 on the left and right sides of the bendable portion 11 of FIG. 3C, in addition application of a positive charge (potential) to the electrode 112 at the top of FIG. 3C, and further in addition to the application of a negative charge (potential) to the electrode 112 at the bottom of FIG. 3C, may result in a different amount of deformation than would occur as a result of the application of a positive charge (potential) on the electrode 112 at the top of FIG. 3C with a negative charge (potential) imparted to the remaining electrodes 112. It will be understood that the user may select the plurality of electrical signals that produces the deformation desired by the user.

FIG. 3D is the cross-sectional view of the bendable portion 11 of FIG. 3A and 3B revealing another embodiment that a second selected set of four electrical signals applied to the circumferentially distributed electrodes 112 disposed about the polymer electrolyte layer 111. FIG. 3D illustrates the application of a positive charge (potential) to the electrode 112 at the top of the bendable portion 11 of FIG. 3D and also to the electrode 112 at the right side of the bendable portion 11 of FIG. 3D, and FIG. 3D further illustrates the application of a negative charge (potential) to the electrode 112 at the bottom of FIG. 3D and also to the electrode 112 at the left side of FIG. 3D. The deformation of the polymer electrolyte layer 111 results from the application of these electrical charges (potentials) is in the direction of the arrow 4.

It will be understood from FIGS. 3C and 3D that the bendable portion 11 of the catheter 1 can be bent in multiple directions and with varying degrees of deformation or deflection by strategic control of the sign (+, −) and magnitude of the electrical charges imparted to each of the individual electrodes 112. Although the embodiment illustrated in FIG. 3A to 3D illustrates a bendable portion 11 including four electrodes 112, it will be understood that the bendable portion 11 of the catheter 1 may include fewer than four or more than four electrodes 112, and such other embodiments will have differing deflection and deformation directional capacities and thus provide more or less degree(s) of freedom.

Figure 4A:
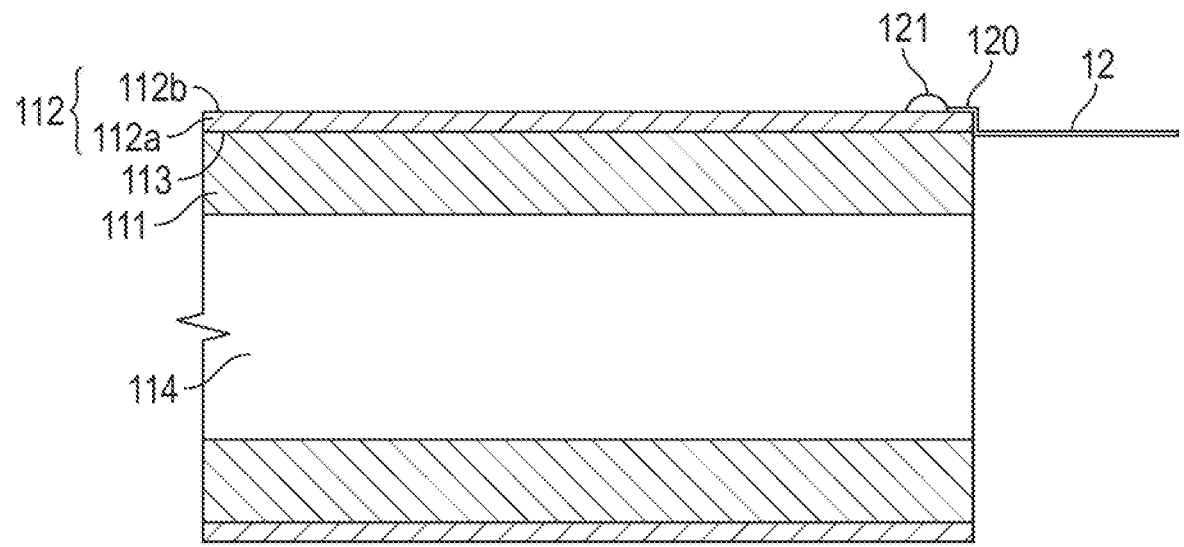
FIG. 4A shows a longitudinal cross section of the ionic electroactive polymer actuator of FIG. 1A according to one embodiment, illustrating interconnection of the electrically-conductive wires and the electrodes.

The electrically-conductive wires 12 can be interconnected with the electrodes 112 in various configurations using any suitable connecting technique. For example, conducting paste or laser welding can be employed to physically and electrically connect the electrically-conductive wires 12 and the electrodes 112. FIG. 4A shows a longitudinal cross section of the ionic electroactive polymer actuator 110 of FIG. 1A, illustrating one embodiment of physical and electrical connection of the electrically-conductive wires 12 and the electrodes 112. The distal ends 120 of the electrically-conductive wires 12 extend along a portion of the surface of the gold layer 112b of each of the electrodes 112 at the proximal end 117 of the ionic electroactive polymer actuator 110 where they terminate in a connection with the electrode 112 using, for example, a small quantity of conductive paste 121.

Figure 4B:
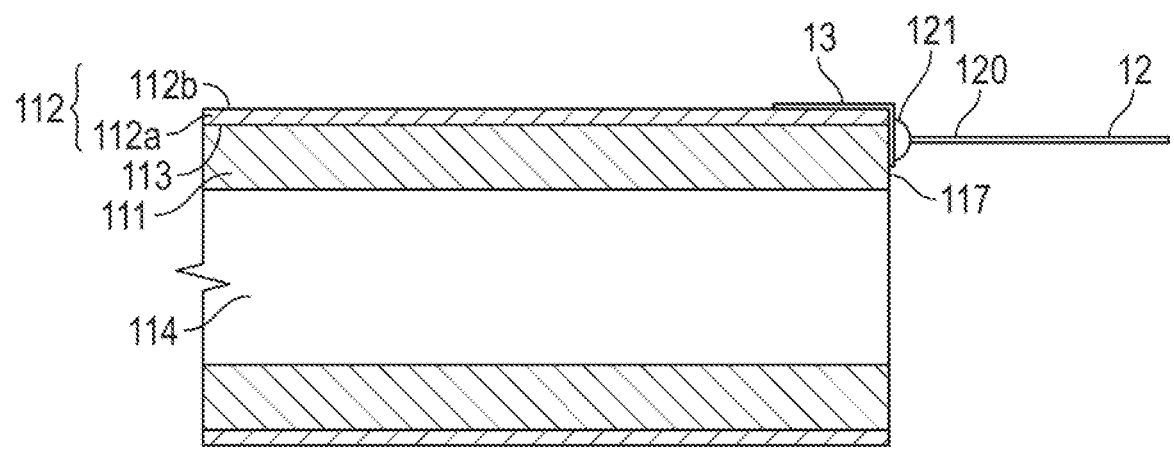
FIG. 4B shows a longitudinal cross section of the ionic electroactive polymer actuator of FIG. 1A according to another embodiment, illustrating interconnection of the electrically-conductive wires and the electrodes via a conductive bridge.
Figure 4C:
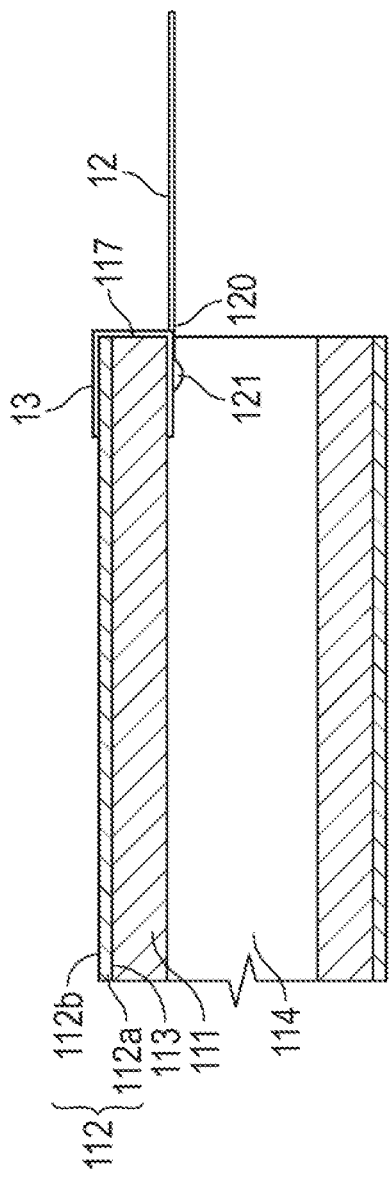
FIG. 4C shows a longitudinal cross section of the ionic electroactive polymer actuator of FIG. 1A according to another embodiment, illustrating another interconnection of the electrically-conductive wires and the electrodes via a conductive bridge.
Figure 4D:
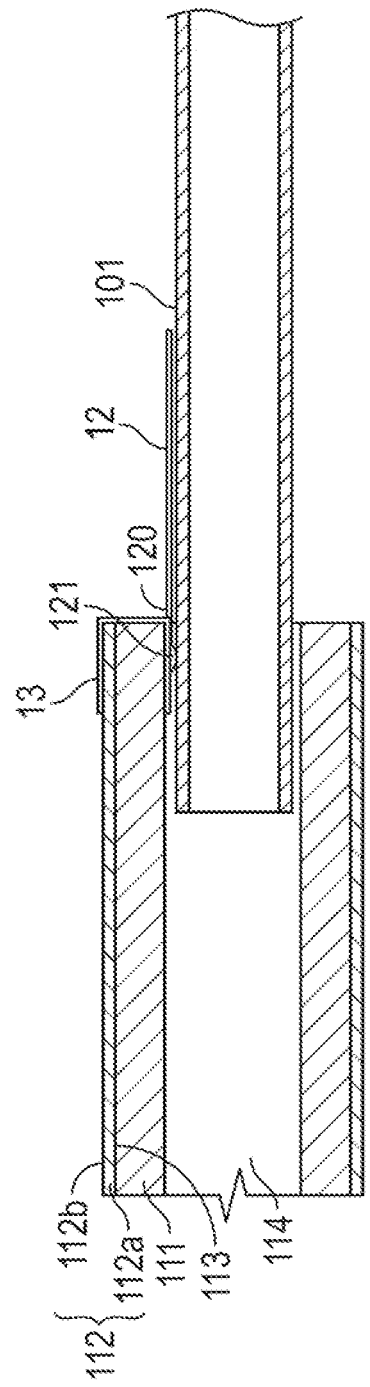
FIG. 4D shows a longitudinal cross section of the ionic electroactive polymer actuator and the liner of FIG. 1A according to one embodiment, illustrating interconnection of the electrically-conductive wires, the liner and the electrodes via a conductive bridge.

Alternatively, FIGS. 4B to 4D illustrate other embodiments of physical and electrical connection of the electrically-conductive wires 12 and the electrodes 112. In FIGS. 4B to 4D, a conductive shunt, hereafter a conductive bridge 13, is formed at the proximal end 117 of the ionic electroactive polymer actuator 110 and extends therefrom to the electrodes 112 along the polymer electrolyte layer 111 and facilitates transmission of electrical potential therebetween. The conductive bridge 13 may be plated on the surface of the gold layer 112b and extend to cover a portion (see. FIG. 4B) or all (see FIGS. 4C and 4D) of the sidewall between the electrode and the proximal end 117 of the electrolyte layer 111, as well as the annular end wall of the proximal end 117 of electrolyte layer 111. The distal ends 120 of the electrically-conductive wires 12 are physically and electrically connected to any location of the conductive bridge 13. In some embodiments, as shown in FIG. 4D, the electrically-conductive wire 12 and the support member 102 are first located over the exterior surface 101 of the liner 101 from the proximal end 103 (see, e.g. FIG. 1A) to the distal end 100 thereof, and then a portion of the electrically-conductive wire 12 and the liner 101 thereunder are embedded into a portion of the bore 104 to electrically connect the wire 12 and the conductive bridge 13. In some embodiments, the conductive bridge 13 can be prepared by applying any conductive foil or tape made of metallic materials (e.g. gold, silver or copper) or non-metallic materials comprising conductive polymers onto the surface of the electrodes 112 and the polymer electrolyte layer 111 using any suitable techniques (e.g. using adhesives, coating, plating, etching or depositing, but not limited to this method of application or to these materials).

Figure 5A:
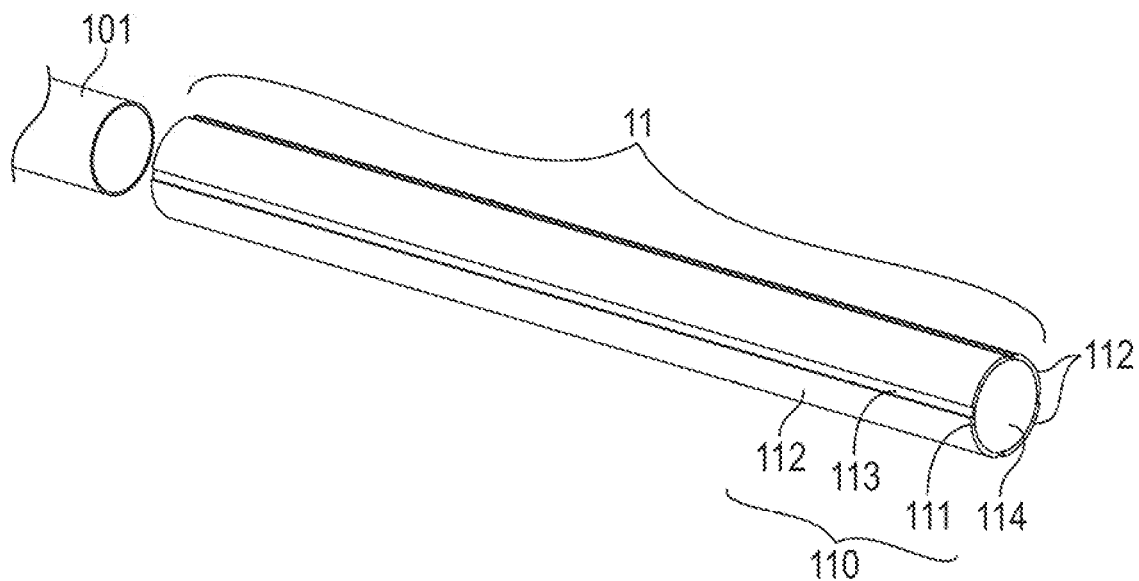
Figure 5B:
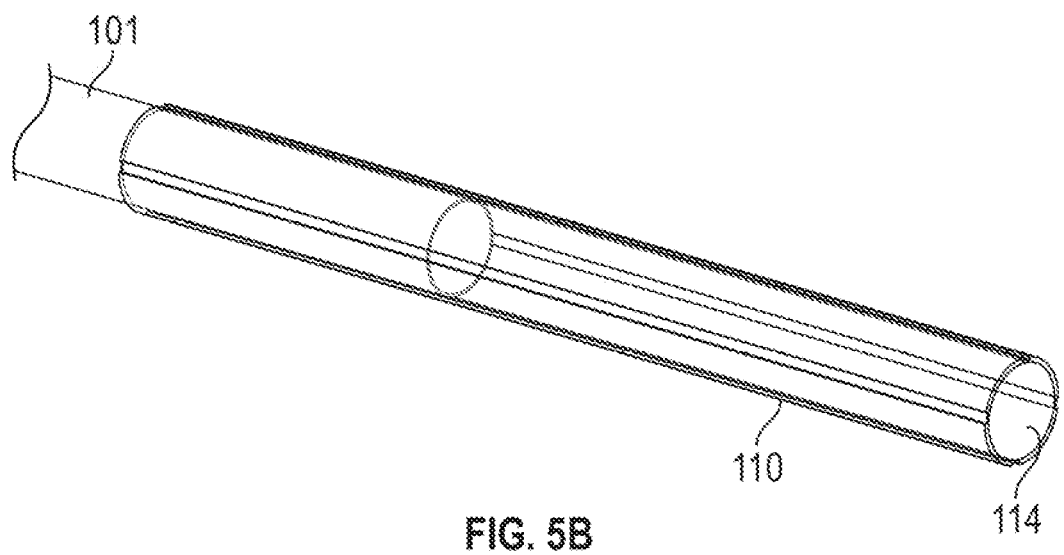

FIGS. 5A to 5E illustrates the integration of the elongate, flexible portion and the bendable portion of a catheter in FIG. 1A according to one embodiment. FIG. 5A is a schematic view of the separate liner and the ionic electroactive polymer actuator. The ionic electroactive polymer actuator 110 can be prepared by depositing electrodes 112 on exterior surface 113 of a polymer electrolyte layer 112 made of a commercial Nafion® tube or a PVDF tube. In other embodiments, the polymer electrolyte layer 112 in a tubular shape can be prepared using a reflow process. The detail of the reflow process is discussed in PCT Application No. PCT/US17/16513, which is fully incorporated herein by reference in its entirety. The electrodes 112 can be deposited using any suitable methods. For example, but not by way of limitation, electrodes 112 made of metal can be deposited (e.g. platinum or gold electrodes) thereon using an electrochemical process. Electrodes 112 made of carbon-based materials can be deposited using the reflow process discussed in PCT Application No. PCT/US17/16513, which is fully incorporated herein by reference in its entirety. In other embodiments, the double-layered electrodes 112 (see, e.g. FIG. 4A to 4D) can be prepared and integrated on the exterior surface 113 by the following steps: spraying the composite layer 112a on the exterior surface 113, spray coating a gold layer 112b on the composite layer 112a, followed by integrating the layers 112a, 112b. As shown in FIG. 5B, the inner liner 101 (e.g. a PTFE liner) may have a smaller outer diameter than the bore 114 of the polymer electrolyte layer 112 do, so that the inner liner 101 can be fitted into the bore 114 such that the inner liner 101 extends inwardly of the bore 114 by about 5 to 10 mm. A parylene encapsulation coating with the thickness of 5 to 10 μm may be coated over the liner 101-bore 114 connection to reinforce the connection thereof.

Figure 5C:
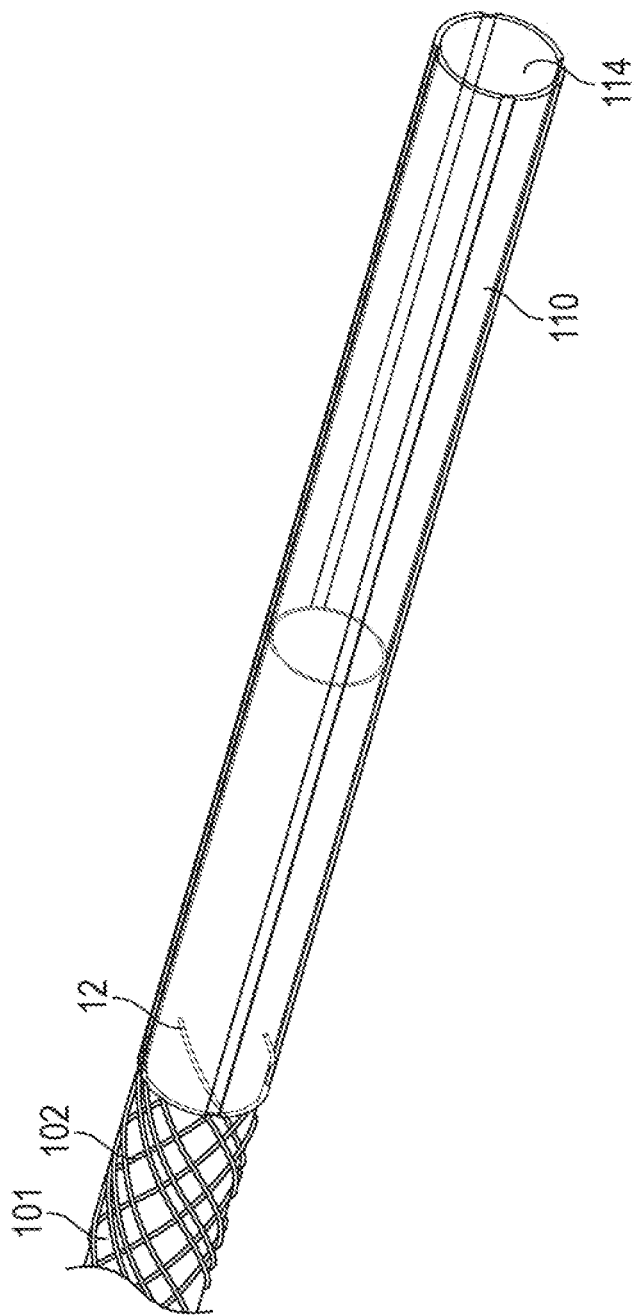
Figures 5D, 5E:
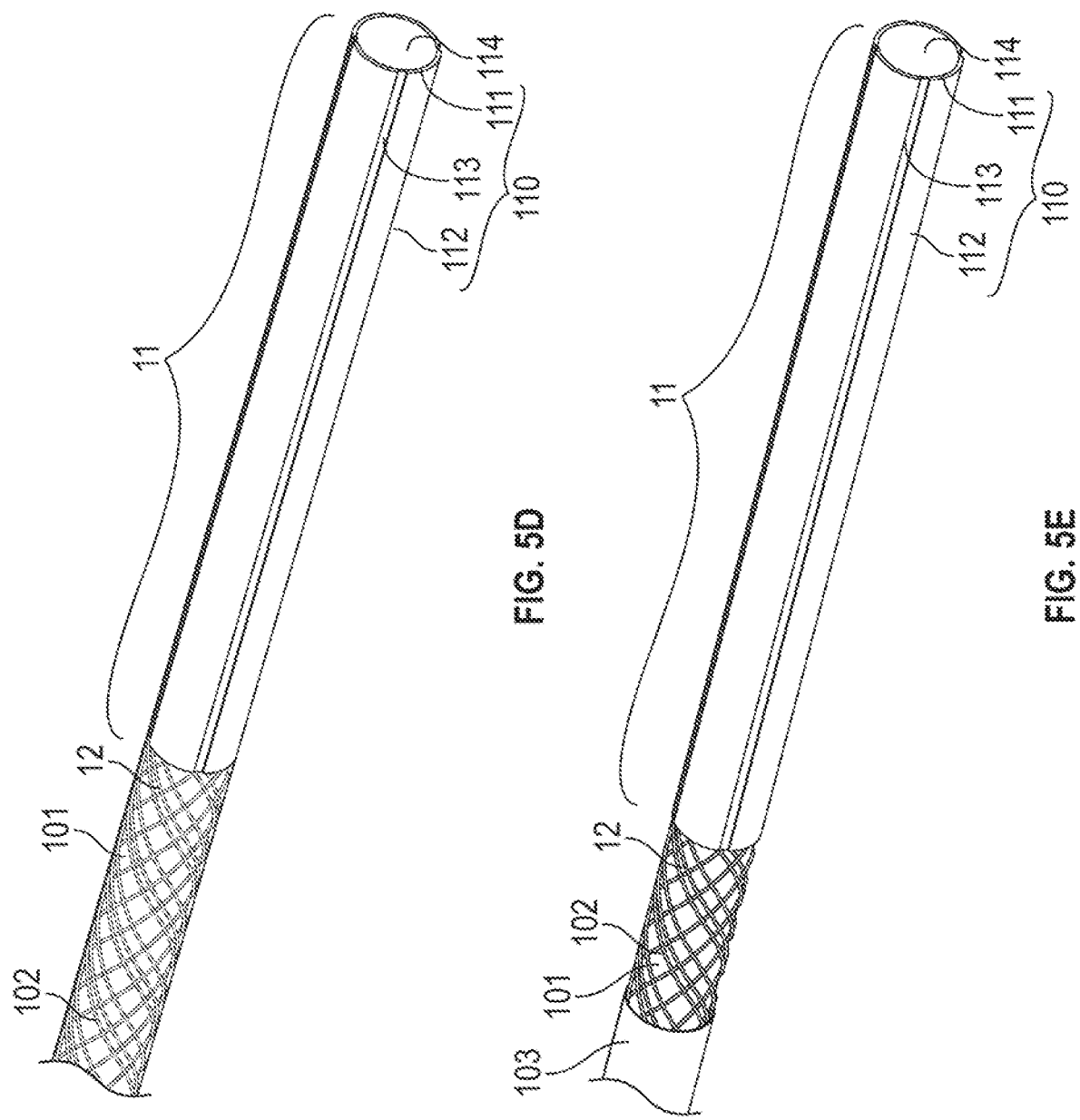

FIGS. 5C and 5D illustrate schematic views of the interconnection of the electrically-conductive wires 12 and the electrodes 112. Any braiding equipment machine and technologies known in the art can be used to braid the electrically-conductive wires 12 and the support member 102 integrally. For example, the braiding process can be performed using a braiding machine that offers vertical continuous reel-to-reel braiding, horizontal reel-to-reel or mandrel braiding. Then, the support member 102 with the electrically-conductive wires 12 braided therein, is slid over the liner 101 as shown in FIG. 5D and attached thereto by an adhesive (e.g., a thermoplastic plastic or thermoset plastic), or by welding, or any combination thereof. After the support member 102 with the electrically-conductive wires 12 thereon is affixed to the liner 101, the distal ends of the electrically-conductive wires 12 extend from at least the distal end thereof. As described above, the distal ends 120 of the electrically-conductive wires 12 extending from the support member 102 can then be coupled to the ionic electroactive polymer actuator 110 directly (e.g. attached to a portion of the surface of the gold layer 112b of FIG. 4A) or indirectly (e.g. through attachment to the conductive bridge 13 shown in FIG. 4B to 4D.) The outer jacket 103 in FIG. 5E is then slid over the support member 102 and the electrically-conductive wires 12, and then secured to the proximal end 117 of the ionic electroactive polymer actuator 110. In some embodiments, a mandrel (not shown), for example, a stainless steel mandrel rod having an outside diameter of 0.025" (0.635 mm) is fitted into the bore 104 and 114 so that the mandrel can support the inner liner 101 and the ionic electroactive polymer actuator 110 for the following assembling using the reflow process. In the reflow process, a heat shrink tube (e.g. a fluorinated ethylene-propylene (FEP) tube) may be positioned over the outer jacket 103 and the ionic electroactive polymer actuator 110 and heat may be applied to cause the heat shrink tube to wrap tightly around the outer jacket 103 and at least the proximal end of the ionic electroactive polymer actuator 110 to firmly secure the outer jacket 103 and the ionic electroactive polymer actuator 110 to one another by squeezing them together. The heat shrink tube and the mandrel is then be removed from the obtained catheter 1 using any suitable technique. For example, the heat shrink tube can be skived.

It is to be noted that various modifications or alterations can be made to the above-described exemplary embodiments of the invention without departing from the technical features of the invention as defined in the appended claims.

We claim:

1. A method for preparing a medical device, comprising:
providing an ionic electroactive polymer actuator comprising a tubular polymer electrolyte layer having a bore and an exterior surface and a plurality of electrodes circumferentially distributed about the exterior surface;
providing an elongate, flexible inner member having a proximal end, a distal end and a bore, wherein the distal end is fitted into a portion of the bore of the tubular polymer electrolyte layer;
providing a mandrel having a diameter of a desired size for the bore of the inner member and the bore of the tubular polymer electrolyte layer and inserting the mandrel into the inner member and the tubular polymer electrolyte layer;
providing a plurality of electrically-conductive wires, each having a proximal end and a distal end;
deploying a plurality of electrically-conductive wires, and braiding each of the electrically conductive wires with a support member, each braided wire having a distal end that extends outwardly of the distal end of the inner member and electrically connecting to one of the electrodes;
locating the support member braided with the electrically-conductive wires over the inner member intermediate of the proximal and distal ends the inner member;
providing an outer member over the inner member and the support member braided with the electrically-conductive wires thereon;
providing a heat-shrink tube; covering the ionic electroactive polymer actuator, the outer member, the support member braided with the electrically-conductive wires and the inner member therein with the heat-shrink tube; and
heating the heat-shrink tube to cause reflow of the polymer film, so that the ionic electroactive polymer actuator, the outer member, the support member braided with the electrically-conductive wires and the inner member therein are secured together; and
removing the mandrel.

2. The method of claim 1, wherein the distal end of each electrically-conductive wire is coupled to a surface of at least one of the electrodes.

3. The method of claim 2, wherein the one or more conductive bridges extends along at least one of the outer surfaces of an electrode, the distal end of an electrode, the distal end of the polymer electrolyte layer, and an interior surface of the flexible inner member.

4. The method of claim 1, further comprising:
forming one or more conductive bridges interfaced with each of the electrodes and the tubular polymer electrolyte layer, so that the distal end of each electrically-conductive wire is coupled to a different one of the conductive bridges.

5. The method of claim 1, wherein the polymer electrolyte layer comprises an electrolyte and a polymer selected from the group consisting of fluoropolymers and intrinsically conducting polymers.

6. The method of claim 5, wherein the fluoropolymers are perfluorinated ionomers, polyvinylidene difluoride (PVDF) or co-polymer thereof.

7. The method of claim 5, wherein the intrinsically conducting polymers comprise polyaniline (PANI), polypyrrole (Ppy), poly(3,4-ethylenedioxythiophene) (PEDOT), poly(p-phenylene sulfide) (PPS) or the combination thereof.

8. The method of claim 1, wherein each of the electrodes comprises one of platinum, gold, carbon-based materials and a combination thereof.

9. The method of claim 8, wherein the carbon-based material comprises one of carbide-derived carbon, carbon nanotube, graphene, a composite of carbide-derived carbon and polymer electrolyte material, and a composite of carbon nanotube and polymer electrolyte material.

10. The method of claim 9, wherein each of the electrodes is formed as a multilayered electrode comprising a carbon-electrode layer comprising the carbon-based material and a gold-electrode layer thereon.

11. The method of claim 10, wherein the gold-electrode layer is formed by a gold nanoparticle dispersion that is applied onto the carbon-electrode layer using a spray coating process.

12. The method of claim 1, wherein the support member is at least one of a reinforcing mesh, a wire-braided matrix and a coil.

13. The method of claim 12, wherein the at least one of a reinforcing mesh, a wire-braided matrix and a coil comprise a plurality of members, spaced from one another in the length direction of the support member.

14. The method of claim 12, wherein the spacing between the plurality of members changes in the length direction of the support member.

* * * * *